United States Patent [19]
Lekhgolts et al.

[11] Patent Number: 5,527,286
[45] Date of Patent: Jun. 18, 1996

[54] SINGLE-USE SYRINGE

[76] Inventors: Victor Lekhgolts, 817 N. Croft Ave. #C, Los Angeles, Calif. 90069; Oleg Shvabsky, 1422 N. Martel Ave. #7, Los Angeles, Calif. 90046

[21] Appl. No.: 462,301

[22] Filed: Jun. 5, 1995

[51] Int. Cl.⁶ ................................................ A61M 5/00
[52] U.S. Cl. ................................ 604/110; 604/218
[58] Field of Search ........................... 604/110, 208, 604/218, 220, 221, 222, 223, 224, 228

[56] References Cited

U.S. PATENT DOCUMENTS

| | | | |
|---|---|---|---|
| 4,775,363 | 10/1988 | Sandsdalen | 604/110 |
| 5,352,203 | 10/1994 | Vallelunga et al. | 604/110 |
| 5,407,436 | 4/1995 | Toft et al. | 604/110 |

*Primary Examiner*—John D. Yasko

[57] ABSTRACT

A single-use syringe has piston (18) mounted in barrel (10) and detachably connected to piston rod (30) though its internal projection (26) engaged by outer projection (36) of elastic leg (34) of the piston rod. Sliding member (48) is mounted in the piston and has cam portion (50). The inside diameter (d) of the sliding member is smaller than the diameter (D) of inside radial face (44) of the internal projection of the piston. The axial length (1) of cam portion (50) of the sliding member is smaller than the axial length (L) of the outer projection of elastic leg (34). When piston rod (30) is moved forward relative to the piston, outer projection (36) of the elastic leg engages the inside face of the sliding member (48) so as to be put into a first position of disengagement from internal projection (26) of the piston and can pass by the internal projection of the piston when the piston rod is moved back relative to the piston so as to put outer projection (36) of the elastic leg into a second disengagement position.

9 Claims, 3 Drawing Sheets

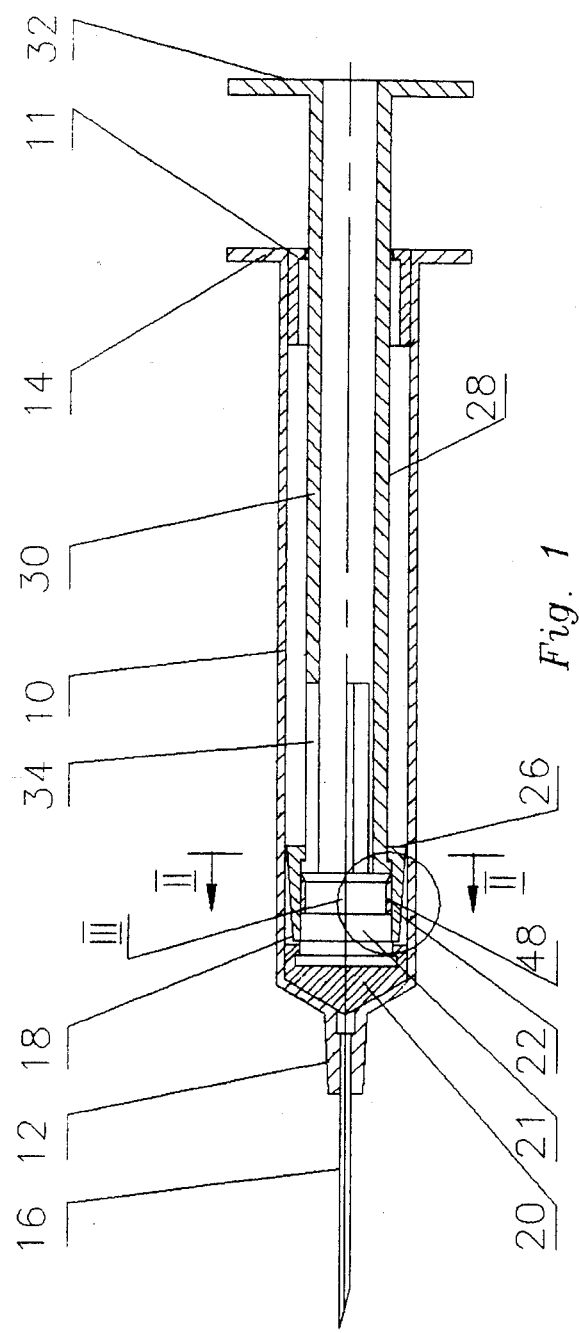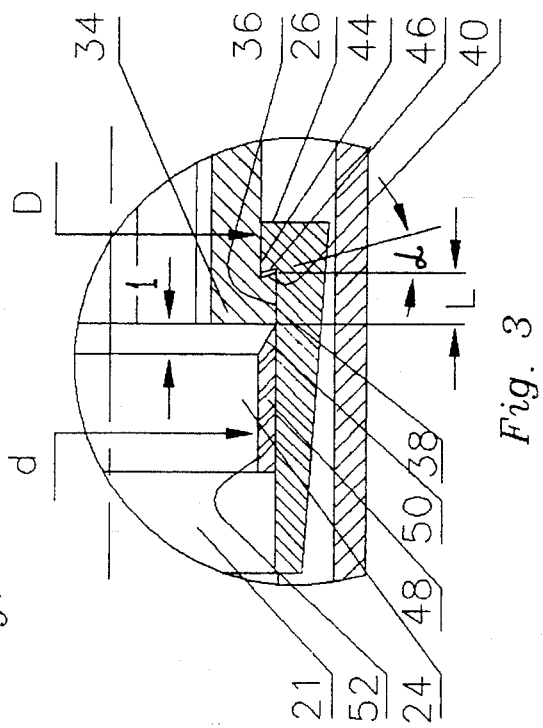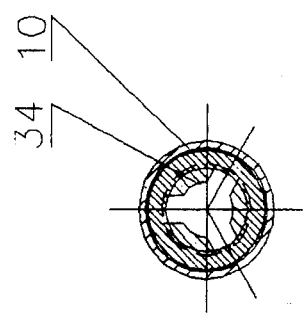

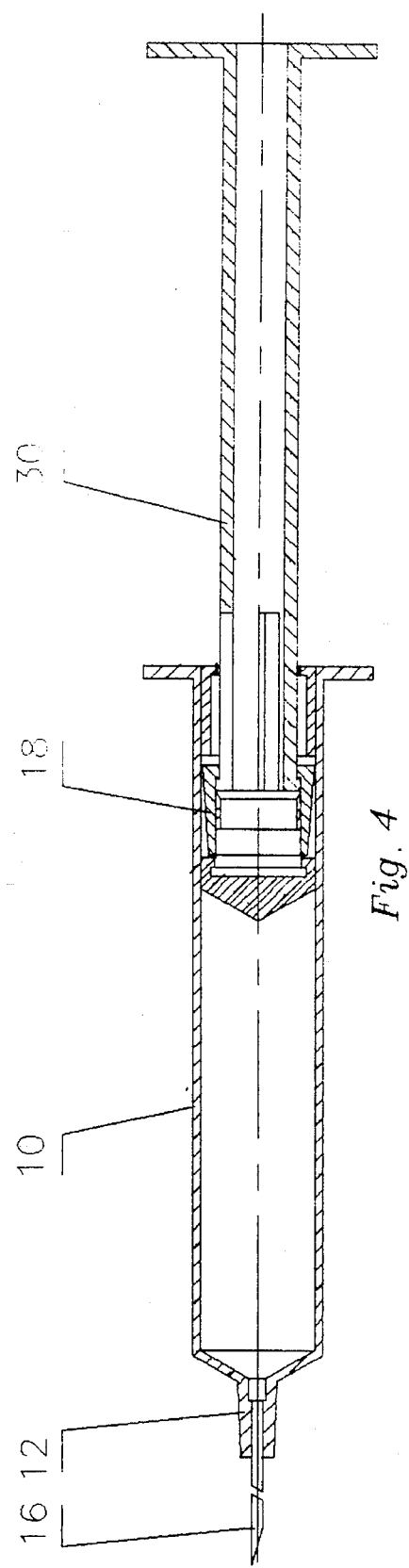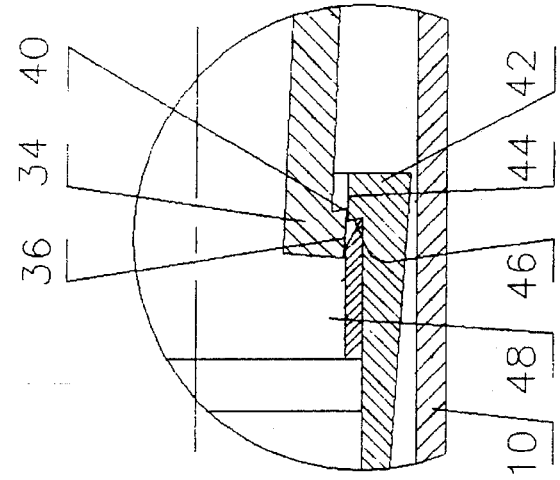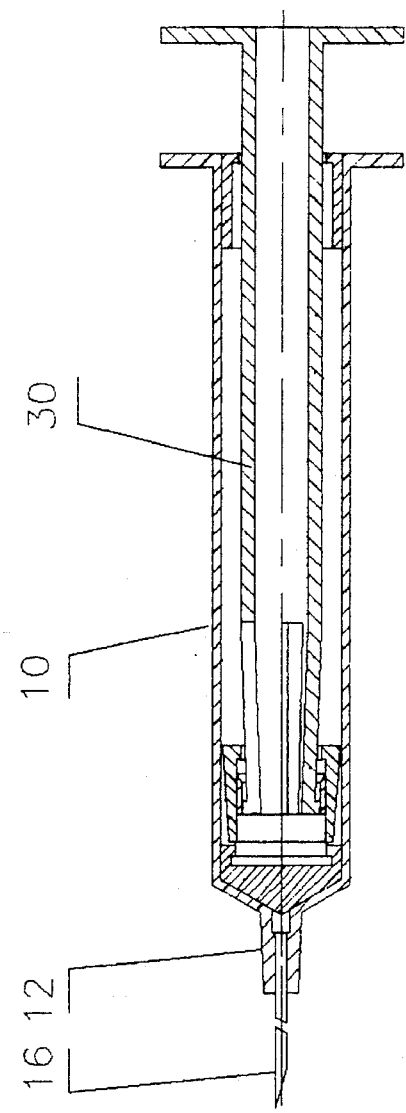

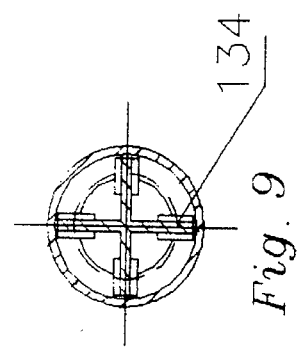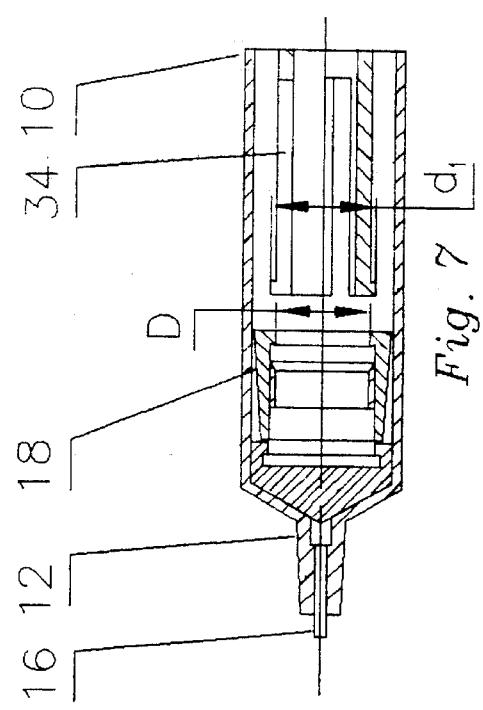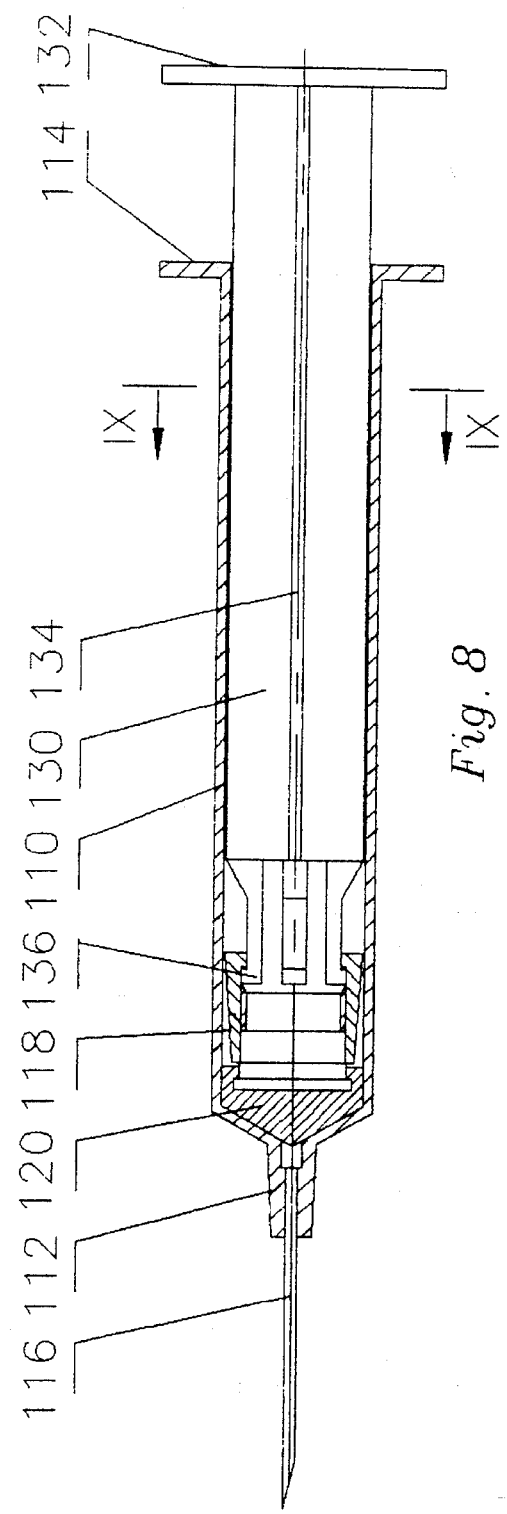

SINGLE-USE SYRINGE

FIELD OF THE INVENTION

The invention relates to the medical field and deals with single-use syringes using a so called safe syringe system. More particularly, the invention relates to syringe systems that become unfit for reuse upon any attempt to reuse. Still more specifically, the invention relates to safety syringe systems that are protected against reuse by a positive separation of the piston and piston actuator or piston rod.

BACKGROUND OF THE INVENTION

A prior art single use syringe has a barrel with a needle, a piston mounted in the barrel for reciprocation, a piston rod mounted in the barrel for moving the piston, and a means for detachably connecting the piston to the piston rod (U.S. Pat. No. 5,389,075). The means for detachably connecting the piston rod to the piston comprises a spring installed between the piston rod and an end wall of the piston and a collar in the form of a half-ring that makes a positive connection between the piston rod and the piston. In this syringe, piston rod is mechanically separated from the piston at the end of it injection stroke, when the spring is compressed to insure a movement of the piston rod relative to the piston. This movement results in a slot between the piston and piston rod opening widely enough for the collar to fall out. As the collar is the only part holding the piston rod and piston together, the piston will remain stationary if an attempt is made to move the piston rod back toward the open end of the barrel so as to fill the syringe for a new injection.

The above-described prior art system has many disadvantages. First, the disconnection of the piston rod from the piston is envisaged during the injection stroke of the piston. This means that some fluid to be injected may be left in the syringe in the event a resistance to injection is greater than the force of spring. The system is not hundred percent proof because fall-out of the collar is not guaranteed as the collar disengages by its own weight. In other words, there is no positive-action disengagement. The collar can get between the piston and the front end of the barrel to hinder the piston movement. In such an event a part of fluid will be left in the barrel and cannot be injected The syringe is not absolutely safe as the piston can be moved back by putting the piston rod askew in the barrel so as to jam the end of the piston rod in the piston for pulling the piston back. The prior art syringe is rather complicated and have too many parts which is not desirable taking into account mass-scale production of such items.

SUMMARY OF THE INVENTION

It is an object of the invention to provide a single-use syringe that insures a reliable protection against reuse.

Another object of the invention is to provide a single-use syringe that is constructed to insure a positive separation of its piston and piston rod in the event of any attempt to reuse.

Still another object of the invention is to provide a single-use syringe that insures complete evacuation of fluid from syringe during injection.

And finally it is an object of the invention to provide a single-use syringe that would have a small number of parts of simple configuration which are easy to manufacture.

Other objects and advantages of the invention will become apparent from the detailed description of its embodiments that follows, with reference to the accompanying drawings.

With these and other objects in view a single-use syringe has a piston mounted in the barrel and detachably connected to a piston rod though its internal projection engaged by an outer projection of an elastic leg of the piston rod. A sliding member is mounted in the piston and has a cam portion. The inside diameter of the ring is smaller than the diameter of the inside radial face of the internal projection of the piston. The axial length of the cam portion of the ring is greater than the axial length of the outer projection of the elastic leg, whereby the outer projection of the elastic leg can engage the inside face of the ring when moved forward relative to the piston so as to be put into a first position of disengagement from the internal projection of the piston and can pass by the internal projection of the piston when moved back relative to the piston so as to put the outer projection of the elastic leg into a second disengagement position.

The above and other objects and advantages of the invention will become apparent from the following detailed description of its preferred embodiments illustrated in the accompanying drawings.

DESCRIPTION OF THE DRAWINGS

FIG. 1 shows a single-use syringe according to the invention in longitudinal section illustrating the syringe in its initial position before filling with an injection fluid;

FIG. 2 is a sectional view taken along line II—II in FIG. 1;

FIG. 3 is an enlarged partial view of an end part of the single-use syringe of FIG. 1;

FIG. 4 shows the syringe of FIG. 1 with the piston moved from its initial position to the end of filling stroke position;

FIG. 5 shows the syringe of FIG. 1 with the piston moved from the filling position to the end of the injection stroke position;

FIG. 6 shows an enlarged detail similar to that shown in FIG. 3 to illustrate the relative position of parts when an attempt is made to refill the syringe after the injection;

FIG. 7 shows the syringe piston and piston rod in the disconnected position;

FIG. 8 another embodiment of a single-use syringe according to the invention in longitudinal section illustrating the syringe in its initial position before filling with an injection fluid;

FIG. 9 is a sectional view taken along line IX—IX in FIG. 8.

DESCRIPTION OF EMBODIMENTS

With reference to FIG. 1, a single-use syringe has a barrel 10 that has a needle receiving end 12 and an opposite open end 14 configured as a flange for a convenient grip. A needle 16 is mounted in needle receiving end 12 of barrel 10 in any appropriate known manner for filling the syringe and for making an injection. A piston 18 is mounted for reciprocation in barrel 10 for movement from one end of stroke position to another between needle receiving end 12 and open end 14 of the barrel. In this particular case piston 18 has a front piston portion 20 that is designed to insure an appropriate sealing of the interior of barrel 10 for filling it with an injection fluid and for its displacement through needle 16. Piston 18 also has a rear portion 22 that is connected to its front portion 20 in any appropriate known manner. With any design of the piston in the syringe, it is important for the piston to have an interior 24. Piston 18 has an internal projection 26 provided at the end of the piston facing toward open end 14 of barrel 10. Projection 26 has the form of an annular projection or is made as an individual protrusion depending on the type of a piston rod used as will be described. A piston rod 28 mounted in barrel 10 in this embodiment has the form of a hollow cylindrical rod 30 that has a flanged portion 32 for a convenient grip. At the end facing toward needle receiving end 12 of the barrel, piston rod 30 has at least one elastic leg 34 protruding from the piston rod in the direction toward piston 18. The drawing in FIGS. 1 and 2 actually shows three such legs 34 defined by a collet end of piston rod 28. It is understood that one or any other number of such legs can be used to achieve the invention results. It will be apparent that the use of more than one leg is better, especially with a large inside diameter of the barrel. At the same time, if a very small single-use syringe is to be made, its piston rod can have one elastic leg.

The single-use syringe according to the invention has a device for detachably connecting piston rod 30 to piston 18 to prevent any reuse of the syringe. According to the invention, this device for detachably connecting the piston rod to the piston is designed to insure a positive separation of the piston and piston rod at any attempt to move the piston rod for refilling the syringe.

The device for detachably connecting the piston rod to the piston has engageable members of the piston and piston rod and a cam portion. As shown in FIGS. 1 and 3, elastic leg 34 has an outer projection 36 that has an outside radial face 38 and an end face 40 on the piston rod side. Internal projection 26 of piston 18 defines a piston shoulder 42. Piston shoulder 42 has an inside radial face 44 and an end face 46 facing toward needle receiving end 12 of the barrel. It can be seen from FIGS. 1 and 3 showing the syringe in its initial position of shipment (before filling with an injection fluid) that piston rod 28 is physically connected to piston 18. Piston 18 can be moved toward the open end of barrel 10 for filling the syringe by gripping piston rod 30 at its flange 32 and pulling it in the direction away from needle receiving end 12. This movement of piston 18 is possible by virtue of engagement of outer projection 36 of elastic leg 34 with internal piston shoulder 42 defined by internal projection 26 of piston 18. End faces 40 and 46 of piston 18 and outer projection 36, respectively, can extend in the diametrical plane of the barrel. With a proper choice of material and treatment, such form of the end faces can insure a rather reliable engagement of the piston and piston rod for the above-mentioned pulling action. It is also understood that the elasticity of leg 34 (that will be explained later on) urges the outer projection radially outwardly and provides a force necessary for holding end faces 40 and 46 together. At the same time, it is preferred that end faces 40 and 46 be inclined at a sharp angle $\alpha$ in the direction toward needle receiving end 12 of barrel 10 as shown in FIG. 3. This angle can be small enough (from 5° to 10°) to positively guarantee the above-described engagement.

It will be apparent from what has been described that when piston rod 28 is pulled back toward the open end of barrel 10, piston 18 will move in the barrel with the piston rod to a position shown in FIG. 4 so as to fill the syringe through needle 16 with an injection fluid. In the position shown in FIG. 4, the syringe is ready for injection.

The device for detachably connecting the piston to the piston rod also has a sliding member in the form of a ring 48 mounted for a limited axial movement within interior 24 of piston 18. The limited movement means that ring 48 in its movement to the left in FIG. 3 will come to bear against a shank portion 21 of piston 18. Ring 48 has a cam portion in the form of a chamfer 50 that has an axial length "l". This axial length "l" of the cam or chamfer portion is chosen to be smaller than an axial length "L" of outer projection 36 of elastic leg 34. Ring 48 has an inside face 52 of a diameter "d" (FIG. 3). This diameter "d" of inside face 52 of ring 48 should be smaller than a diameter "D" of inside face 44 of piston shoulder 42.

When piston 18 is at the very beginning of its injection stroke and the parts are in the position shown in FIG. 3, further movement of piston rod 28 toward needle receiving end 12 of barrel 10 results in piston rod 28 moving relative to piston 18. This is due to the resistance to flow of fluid through needle 16 during injection. In this relative movement, elastic leg 34 moves to the left in FIG. 3, along cam portion 50 of ring 48 that will come to bear against shank 21 of front portion 20 of piston 18 (FIG. 5). This movement of elastic leg 34 will result in its bending, whereby outside radial face 38 of projection 36 of the elastic leg will engage inside radial face 52 of ring 48, and outside radial face 38 will be at a diameter smaller than diameter "D" of inside radial face 44 of piston shoulder 42. In this position there is no engagement between end faces 40 and 46 of piston shoulder 42 and the outer projection of leg 34. This means that in the event an attempt is made to pull piston rod 28 again in the direction toward open end 14 of barrel 10, a friction between outside radial face 38 of the outer projection of leg 34 and inside radial face 52 of ring 48 will result in leg 34 dragging ring 48 to the right until the ring comes to a positive stop against end face 46 of piston shoulder 42, outside radial face 38 of the outer projection of leg 34 will pass by piston shoulder 42 without, however, engaging it due to the difference of diameters "d" and "D" as described above (the position is shown in FIG. 6). Moving further, outside radial face 38 of elastic leg 34 will drag over inside radial face 44 of piston shoulder 42 in its movement to the right in FIG. 6. Having passed to the end of inside radial face 44 of piston shoulder 42, elastic leg 34 will be free to move by its own elasticity to its free unrestrained position. As a result, there will be no physical connection between piston rod 28 and piston 18 as shown in FIG. 7, with a diameter "$d_1$" of outside radial face 38 being greater than diameter "D" of inside radial face 44 of piston shoulder 42. This means piston rod 28 cannot be reconnected to piston 18 for moving the piston toward the open end of barrel 10.

The term "elastic leg" used throughout the entire description means that leg 34 is made of an elastic material such as plastic. Before the assembly of the syringe, elastic leg 34 is in the position shown in FIG. 7. When the syringe is assembled, leg 34 is slightly bent inwardly to insert it into piston 18 and to bring it into engagement with piston shoulder 42 as shown in FIG. 3. Also with reference to assembly of the syringe according to the invention, it will be apparent that ring 48 has to be inserted into rear part 22 of piston 18. Front part 20 of piston 18 is then forced into, or otherwise secured in rear part 22 of the piston to insure proper sealing and reliable fastening. Elastic leg 34 is then bent inwardly for engagement with piston shoulder 42, and the entire assembly is inserted into barrel 10 at its open end 14. It is understood that various parts of the syringe are made of appropriate materials, typically of plastics as well known to those skilled in the art. It will also be apparent that no metal parts are required (except for the needle) for the construction of this invention.

Although reference was made throughout the description to an elastic leg 34, it will be apparent that all elastic legs 34 will work in the same manner as described above for one elastic leg 34.

The embodiment of syringe shown in FIG. 1 and described above has hollow cylindrical piston rod 28 with a collet at the end defining elastic legs 34. A guide 11 at the open end of barrel 10 is used for insuring a smooth movement of piston rod 28. In the embodiment shown in FIG. 8 a barrel 110 has a needle receiving end 112 and an open end 114. A needle 116 is received in needle receiving end 112 of the barrel. A piston 118 with its front portion 120 is mounted in barrel 110 and is connected to a piston rod 130. Piston rod 130 has a flanged portion 132 and is solid, with ribs 134 (FIGS. 8, 9). Elastic legs 136 are made as projections of piston rod 130 extending in the axial direction. For the rest, the construction and operation of the syringe shown in FIGS. 8, 9 are similar to the syringe described with reference to FIGS. 1 through 7.

Various changes and modifications can be made in the construction of the above described syringe. Thus elastic legs of the piston rod can be made as separate parts, and the piston rod itself may be of a different cross-sectional configuration. Elastic legs can be formed, e.g., by cutting the end portion of the piston rod. The cam portion of the sliding member or ring can have a different form, e.g., it can be in the form of a curvilinear face. All these changes and modifications do not go beyond the spirit and scope of the invention as defined in the appended claim.

We claim:

1. A single-use syringe comprising a barrel having a needle receiving end and an open end, a needle mounted in said needle receiving end of said barrel, a piston mounted in said barrel for reciprocation in said barrel to perform strokes between said needle receiving end and said open end of said barrel, said piston having an end facing toward said open end of the barrel, a piston rod for moving said piston in said barrel, a means for detachably connecting said piston rod to said piston, said connecting means comprising:

an internal projection at said end of said piston facing toward said open end of said barrel, said internal projection defining a piston shoulder that has an inside radial face and an end face facing toward said needle receiving end of said barrel;

at least one elastic leg protruding from said piston rod in the direction toward said piston, said at least one elastic leg having an outer projection that has an inside face and an axial length;

an outer projection of said at least one elastic leg of said piston rod having an outside radial face and an end face, said end face of said outer projection engaging said end face of said piston shoulder when said piston is in its initial position at the needle receiving portion of said barrel so as to physically connect said piston to said piston rod for a combined movement of said piston with said piston rod from said initial position toward said open end of said barrel;

a sliding member mounted in said piston for a limited axial movement in said piston, said sliding member having an inside face, said outside radial face of said outer projection of said at least one elastic leg of said piston rod being engageable with said inside face of said sliding member upon movement of said piston rod relative to said piston in the direction away from said open end of said barrel;

a cam portion on said sliding member, said cam portion being engageable with said at least one elastic leg of said piston rod, said cam portion being axially shorter than said axial length of said outer projections of said at least one elastic leg of said piston rod, whereby said at least one elastic leg of said piston rod is caused to move radially inwardly at the beginning of stroke of said piston away from said open end of said barrel to a first disengagement position, in which said at least one elastic leg of said piston rod is retained due to said engagement of said outside radial face of said outer projection of said at least one elastic leg of said piston rod with said inside face of said sliding member, whereby said inside face of said outer projection of said at least one elastic leg of said piston rod can move past said inside radial face of said piston shoulder to a second position of disengagement of said outer projection of said at least one elastic leg of said piston rod from said piston shoulder in which said outer projection of said at least one elastic leg of said piston rod is located radially outwardly with respect to said inside radial face of said piston shoulder upon the beginning of a second stroke of said piston toward said open end of said barrel.

2. The single-use syringe of claim 1, wherein said sliding member comprises a ring that has an inside face of a diameter which is smaller than the diameter of said inside radial face of said internal projection of said piston, said ring having an inner chamfer at the end thereof facing toward said open end of said barrel, the outside diameter of said outside radial face of said outer projection of said at least one elastic leg of said piston rod in said second disengagement position being greater than the inside diameter of said inside radial face of said internal projection of said piston.

3. The single-use syringe of claim 1, wherein said end face of said piston shoulder and said end face of said outer projection of said at least one elastic leg of said piston rod are inclined to extend at a sharp angle in the direction toward said needle receiving end of said barrel.

4. The single-use syringe of claim 1, wherein said end face of said piston shoulder is inclined to extend at a sharp angle in the direction toward said needle receiving end of said barrel.

5. The single-use syringe of claim 1, wherein said end face of said outer projection of said at least one elastic leg of said piston rod is inclined to extend at a sharp angle in the direction toward said needle receiving end of said barrel.

6. A single-use syringe comprising a barrel having a needle receiving end and an open end, a needle mounted in said needle receiving end of said barrel, a piston mounted in said barrel for reciprocation in said barrel to perform strokes between said needle receiving end and said open end of said barrel, said piston having an end facing toward said open end of the barrel, a piston rod for moving said piston in said barrel, a means for detachably connecting said piston rod to said piston, said connecting means comprising:

an internal projection at said end of said piston facing towards said open end of said barrel, said internal projection defining a piston shoulder that has an inside radial face and an end face facing toward said needle receiving end of said barrel;

a collet at the end of said piston rod facing toward said needle receiving end of said barrel, said collet defining a plurality of elastic legs each having an outer projection having an inside face, an outside radial face, an end face, and an axial length, said end faces of said outer projections engaging said end face of said piston shoulder when said piston is in its initial position at the needle receiving portion of said barrel so as to physically connect said piston to said piston rod for a combined movement of said piston with said piston rod from said initial position toward said open end of said barrel;

a ring mounted for a free movement in said piston, said ring having an inside radial face of a diameter which is smaller than the diameter of said inside face of said internal projection of said piston and an inner chamfer at the end thereof facing toward said open end of said barrel, the outside diameter of said outside face of said outer projections of said legs of said piston being greater than the inside diameter of said inside radial face of said internal projection of said piston when said piston rod is disengaged from said piston, said chamfer being axially shorter than said axial length of said outer projections of said elastic legs of said piston rod.

7. The single-use syringe of claim 5, wherein said end face of said piston shoulder and said end face of said outer projections of said elastic legs of said piston rod is inclined at a sharp angle in the direction toward said needle receiving end of said barrel.

8. The single-use syringe of claim 1, wherein said end face of said piston shoulder is inclined to extend at a sharp angle in the direction toward said needle receiving end of said barrel.

9. The single-use syringe of claim 1, wherein said end face of said outer projection of said at least one elastic leg of said piston rod is inclined to extend at a sharp angle in the direction toward said needle receiving end of said barrel.

* * * * *